US008697951B2

(12) United States Patent
Carree et al.

(10) Patent No.: US 8,697,951 B2
(45) Date of Patent: Apr. 15, 2014

(54) CYTOPLASMIC MALE STERILE RUCOLA

(75) Inventors: Franciscus Hermanus Carree, Nootdorp (NL); Petrus Lambertus Josephus Egelmeers, Oud Gastel (NL); Wilhelmus Petrus Adrianus Roeland Voermans, Etten-Leur (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 610 days.

(21) Appl. No.: 12/911,612

(22) Filed: Oct. 25, 2010

(65) Prior Publication Data

US 2011/0078815 A1 Mar. 31, 2011

Related U.S. Application Data

(63) Continuation-in-part of application No. PCT/EP2009/054966, filed on Apr. 24, 2009.

(30) Foreign Application Priority Data

Apr. 24, 2008 (EP) .................................... 08007941

(51) Int. Cl.

| | |
|---|---|
| ***A01H 5/10*** | (2006.01) |
| ***A01H 5/00*** | (2006.01) |
| ***A01H 1/04*** | (2006.01) |
| ***A01H 1/02*** | (2006.01) |
| ***A01H 5/12*** | (2006.01) |

(52) U.S. Cl.
USPC ........... 800/303; 800/306; 800/274; 800/269; 800/268; 800/305

(58) Field of Classification Search
None
See application file for complete search history.

(56) References Cited

FOREIGN PATENT DOCUMENTS

| | | |
|---|---|---|
| GB | 2 211 205 | 6/1989 |
| WO | WO 96/21010 | 7/1996 |
| WO | WO 2008/084329 | 7/2008 |

OTHER PUBLICATIONS

Agnihotri et al. (1990, Plant Breeding 104: 281-289).*

Kumar et al. (1986, Indian Journal of Agricultural Sciences 56: 229-233).*

Grelon, et al., Ogura Cytoplasmic Male-Sterility (CMS)-Associated . . . ; Mol Gen Genet (1994) vol. 243, p. 540-547.

Hanson, et al., Interactions of Mitochondrial and Nuclear Genes That Affect Male Gametophyte Development, The Plant Cell (2004) vol. 16, p. S154-S169.

Hinata, et al., *Brassica campestris, Diplotaxis muralis*, Japan. J. Breed (1979) vol. 29, No. 4, p. 305-311.

Y. Matsuzawa, et al., Male Sterility in Alloplasmic *Brassica rapa* L. Carrying . . . ; Plant Breeding (1999) vol. 118, p. 82-84.

R. Pellan-Delourme, et al., Identification of Maintainer Genes in *Brassica napus* L., Plant Breeding (1987) vol. 99, p. 89-97.

Georges Pelletier, et al., The Molecular Biology of Cytoplasmically Inherited Male Sterility . . . , Curr. Opinion in Biotechnology (2007) vol. 18, p. 121-125.

M.A. Sigareva, et al., Direct Transfer of a Cold-Tolerant Ogura Male-Sterile . . . , Theor Appl Genet (1997) vol. 94, p. 213-220.

S.C. Verma, et al., Genic Male Sterility in *Eruca sativa* Cruciferae, Incompat. Newsl. (1984) vol. 16, p. 9.

Thomas W. Walters, et al., Protoplast Fusion-Derived Ogural Male Sterile . . . , Plant Cell Reports (1992) vol. 10, p. 624-628.

* cited by examiner

*Primary Examiner* — David T Fox
*Assistant Examiner* — Jared Shapiro
(74) *Attorney, Agent, or Firm* — Vedder Price P.C.; Thomas J. Kowalski; Deborah L. Lu

(57) ABSTRACT

The present invention relates to a male sterile Rucola plant obtainable by a method which may comprise the steps of providing fertile pollen from *Eruca sativa* to the stamen of plants that contain CMS cytoplasm, allowing plant embryo's to develop, isolating the embryo's, raising the embryo's in tissue culture to produce plant lets, growing plants from the plantlets; selecting plants that are male sterile and female fertile; backcrossing these plants with fertile pollen from *Eruca sativa*; selecting a plant that is male sterile and female fertile; and optionally repeating steps g) and h).

10 Claims, 10 Drawing Sheets

Fig. 1A orfB

OrfB sequence in *Brassica* (CMS/sterile) and *Eruca sativa* (CMS)

GCACAGTAGAGTGCTTTACCTACCAGAGGTATCTATAGAATGAAAGAATCATTTTATGCT
TCCTTGGCCATGTACAGCATGGATTAGCATTATGTCATTCCTACAATTCCTACAAGTGAT
CCACCTTCCAGTATTTGAAGGAGAGGACTTCGATAGATTATATAATATGTTTCTTTCCAT
TCCTCGTGAGCCACTTATTTCTCCGAAACAAGAGATCAAAGTGATTTTCCTCCTTTTTCC
CAATAAGTCGACGGCCTTACACCATTGGGATACTTCGAATAAACTAGCATACATATAGGA
TACACCAGTGCTAAAACCTTTTCTCAAGAGATCTTCCAAACTGTTGGGGTCCTTGCTCTG
GATGGTCTTCCCCCGGTGTGAAAGCAGTTGGTTCCGTAGTTTTAGAATTCTGCTGATCCC
AAGTACTCCATCTCCATCATTGCATATGAAAATATAGAAAGTAAAGAAGAAAAGGCATAA
CCAGAAGAATTGTGAAAAATAAGTGAATTTATCCAGTTGAGGCAT
GATTAGATTAATTGATTTCAACAAATCCCTCCAGACAGCTTCA

OrfB sequence in *Eruca sativa* (fertile)

GCGGACTTGACGTCATCCCCCACCTTCCTCAGTATATCACTGGCAGTCCCTCGTGAGTGC
GTCACGCACCTTTTTGTTTGTTTCGGAGCGGTTTTGTCAGGGCGTACTAAACCCACTTCC
TTCGTCCCACACCACCGTTCGGCTCACCTGAATGCCGAGTCTTTCTCCGCCGACTAGTTA
GGGCTTGGAAAGGCGCCGGAGGAACCCCTTGTTACTGAGAGCAGAGCTAGTTGCTGTCAC
TCAATTCCTAGGTCTGGCACATCACTCGGCTACTTGGCTTACTTCGGTTTGCACAACCTT
TCTCCTTAGGCGCATGTCTGAGCAACACAAGGCGAGGGTTTCGCTCGTTATAGGACTTAA
CCAAACATCTCACGACACGAGCTGACGACAGCCATGCAGCACCTGTATGAAAGTCAGTAC
CATCCCGTTAAAGACAGGTTTTGTTGTTCA

Fig. 2 orf138

Orf138 sequence in *Brassica* (CMS/sterile) and *Eruca sativa* (CMS)

AGTGACAATACCGCTTTTCTTCAGCATATAAATGCAATGATTACCTTTTTCGAAAAATTG
TCCACTTTTTGTCATAATCTCACTCCTACTGAATGTAAAGTTAGTGTAATAAGTTTCTTT
CTTTTAGCTTTTTTACTAATGGCCCATATTTGGCTAAGCTGGTTTTCTAACAACCAACAT
TGTTTACGAACCATGAGACATCTAGAGAAGTTAAAAATTCCATATGAATTTCAGTATGGG
TGGCTAGGTGTCAAAATTACAATAAAATCAAATGTACCTAACGATGAAGTGACGAAAAAA
GTCTCACCTATCATTAAAGGGGAAATAGAGGGGAAAGAGGAAAAAAAAGAGGGGAAAGGG
GAAATAGAGGGGAAAGAGGAAAAAAAAGAGGGGAAAGGGGAAATAGAGGGGAAAGAGGAA
AAAAAAGAGGTG

In *Eruca sativa* (fertile): no PCR product

Fig. 3A

MTV7

MTV7 sequence in *Brassica* (CMS/sterile) and *Eruca sativa* (CMS)

GCGGACTTGACGTCATCCCCCACCTTCCTCAGTATATCACTGGCAGTCCCTCGTGAGTGC
GTCACGCACCTTTTTGTTTGTTTCGGAGCGGTTTTGTCAGGGCGTACTAAACCCACTTCC
TTCGTCCCACACCACCGTTCGGCTCACCTGAATGCCGAGTCTTTCTCCGCCGACTAGTTA
GGGCTTGGAAAGGCGCCGGAGGAACCCAGCTTCTCCCCTAAAGGAGGAACCCCTTGTTAC
TGAGAGCAGAGCTAGTTGCTGTCACTCAATTCCTAGGTCTGGCACATCACTCGGCTACTT
GGCTTACTTCGGTTTGCACAACCTTTCTCCTTAGGCGCATGTCTGAGCAACACAAGGCGA
GGGTTTCGCTCGTTATAGGACTTAACCAAACATCTCACGACACGAGCTGACGACAGCCAT
GCAGCACCTGTATGAAAGTCAGTACCATCCCGTTAAAGACAGGTTTTGTTGTTCA

MTV7 sequence in *Eruca sativa* (fertile)

GCGGACTTGACGTCATCCCCCACCTTCCTCAGTATATCACTGGCAGTCCCTCGTGAGTGC
GTCACGCACCTTTTTGTTTGTTTCGGAGCGGTTTTGTCAGGGCGTACTAAACCCACTTCC
TTCGTCCCACACCACCGTTCGGCTCACCTGAATGCCGAGTCTTTCTCCGCCGACTAGTTA
GGGCTTGGAAAGGCGCCGGAGGAACCCCTTGTTACTGAGAGCAGAGCTAGTTGCTGTCAC
TCAATTCCTAGGTCTGGCACATCACTCGGCTACTTGGCTTACTTCGGTTTGCACAACCTT
TCTCCTTAGGCGCATGTCTGAGCAACACAAGGCGAGGGTTTCGCTCGTTATAGGACTTAA
CCAAACATCTCACGACACGAGCTGACGACAGCCATGCAGCACCTGTATGAAAGTCAGTAC
CATCCCGTTAAAGACAGGTTTTGTTGTTCA

Fig. 4A

NAD7

NAD7 sequence in *Brassica* (CMS/sterile) and *Eruca sativa* (CMS)

GGTCGAAACGGACGAAAACGAAACTTTACGACAGCTTTTTCGTACACGTTCACTTGCATC
ACATACACAAGTGCTCTCTGAACCGTGCAATAAGGTCACCCATAACACGGCTCTCCCACT
TGAGTGATTTTAGCCCCAGGCCATGCTATTCAATGATATTGGAAAAATGGCAGCGTAACG
TAAGAACTAGTATTGAAAGCTAGTCCCCTTTTGAGGGAGGGAAAGCCTTTCAATAGAAGC
CCTACTTCCCGAGGTATTTCTTACTCGACTGAAAGGAGAGGAACGCCTCATCACTTCAAT
TGTTGCGCAAACCAATTTCTTTCTTAGTCACCGGGCGGAGCGCGCTTTTGGTACTTTGCT
TATAGCTTTTTAGGTTATGCAATAGAAGGGAGGCAACGCTCTGGGCTTGCAGAAATGAAT
GGATCAGAAAGAGGGGGGGCTGGATTCAATTTCCAGGCCGGGCGGGAGGTGAAGACCAT
AAGAGAAGATTGCCCTCCCGGCAAGGCGTTCCTCGGCGTTCCTCGGCGCTGTCATCTATC
TCGACCCATTCCCTGATTTTCTCTGTATGAGGACCTCCTTCCCTTCTGCCCACTCTCCGT
TCACACAGTTCTCAAAGCAGAGGAGGAAGGGTGGGCAGAAGGTACCACGAGCCCTCTGTC
CCACACATCTATCCAGAAGCAAGTGTAGTTCACCGGTTCCACCGAATGCTCCTATCTCTC
GGCAAAGATTGTGTGAGTGTGCAGTTATGCTTCGGATGCTTCGCAATAGATCGACCCAGT
TCCCGTTCTTTTCCGGTGCACTCGCTTTATATCTCCGATACACAGGGAAGGACGCGGTGG
GAAGGGGTTCCTTCGCCCTAGCCTCTGTCCGGCCGATCATTCCGCTGGCATCTTGCATTC
ACGCCTCCGTTTGACTGCCGCTCGGGGATGTAGTTGTAGATACGTTAGTCAACGTGGGTC
GTTGGCTCCACCTGTTCTCTCCTTCTACGACATGCTGTTGTTGTCGCCATATTCCATATG
TCACTTAGTCATCTCTGCCTCGCTGCGGGTCAGCACCTCCGAAAGAAACGGAGGACTCAT

Fig. 4B

NAD7 sequence in *Eruca sativa* (fertile)

GGTCGAAACGGACGAAAACGAAACTTTACGACAGCTTTTTCGTACACGTTCACTTGCATC
ACATACACAAGTGCTCTCTGAACCGTGCAATAAGGTCACCCATAACACGGCTCTCCCACT
TGAGTTATTTTAGCCCCAGGCCATGCTATTCAATGATATTGGAAAAATGGCAGCGTAACG
TAAGAACTAGTATTGAAAGCTAGTCCCCTTTTGAGGGAGGGAAAGCCTTTCAATAGAAGC
CCTACTTCCCGAGGTATTTCTTACTCGACTGAAAGGAGAGGAACGCCTCATCACTTCAAT
TGTTGCGCAAACCAATTTCTTTCTTAGTCACCGGGCGGAGCGCGCTTTTGGTACTTTGCT
TATAGCTTTTTAGGTTATGCAATAGAAGGGAGGCAACGCTCTGGGCTTGCAGAAATGAAT
GGATCAGAAAGAGGGGGGGCTGGATTCAATTTCCAGGTCGGGCGGGAGGTGAAGACCAT
AAGAGAAGATTGCCCTCCCGGCAAGGCGTTCCTCGGCGTTCCTCGGCGCTGTCATCTATC
TCGACCCATTCCCTGATTTTCTCTGTATGAGGACCTCCTTCCCTTCTGCCCACTCTCCGT
TCACACAGTTCTCAAAGCAGAGGAGGAAGGGTGGGCAGAAGGTACCACGAGCCCTCTGTC
CCACACATCTATCCAGAAGCAAGTGTAGTTCACCGGTTCCACCGAATGCTCCTATCTCTC
GGCAAAGATTGTGTGAGTGTGCAGTTATGCTTCGGATGCTTCGCAATAGATCGACCCAGT
TCCCGTTCTTTTCCGGTGCACTCGCTTTATATCTCCGATACACAGGGAAGGACGCGGTGG
GAAGGGGTTCCTTCGCCCTAGCCTCTGTCCGGCCGATCATTCCGCTGGCATCTTGCATTC
ACGCCTCCGTTTGACTGCCGCTCGGGGATGTAGTTGTAGATACGTTAGTCAACGTGGGTC
GTTGGCTCCACCTGTTCTCTCCTTCTACGACATGCTGTTGTTGTCGCCATATTCCATATG
TCACTTAGTCATCTCTGCCTCGCTGCGGGTCAGCACCTCCGAAAGAAACGGAGGACTCAT

Figure 5A:
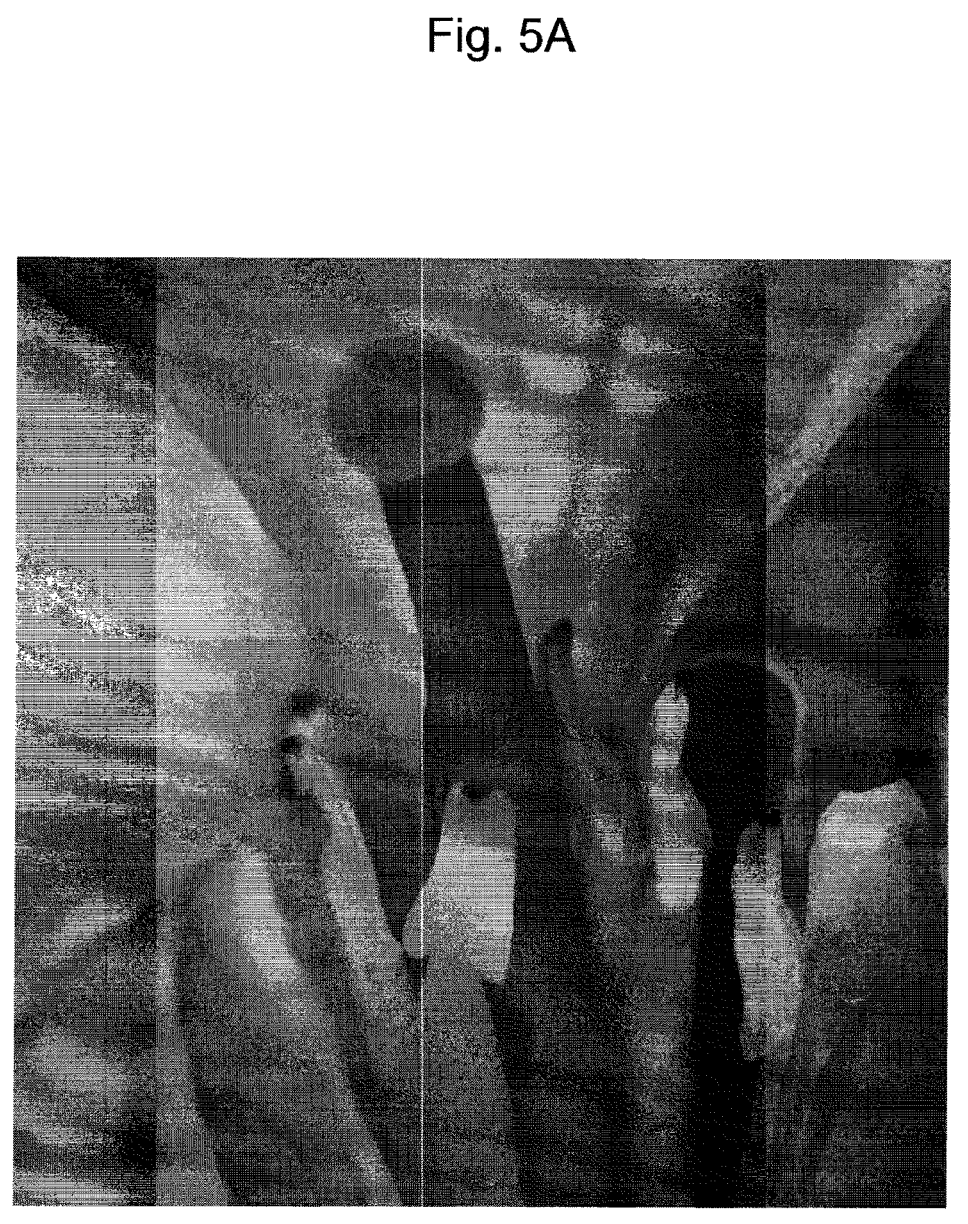

Figure 8:
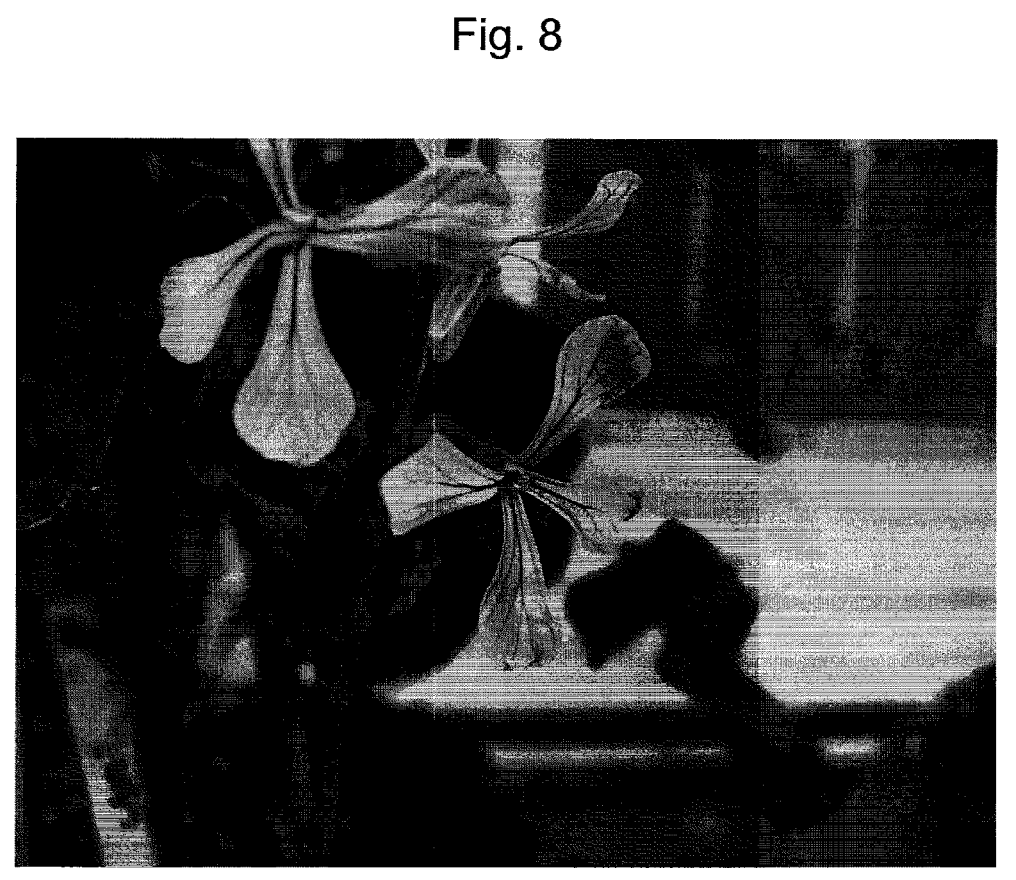

CYTOPLASMIC MALE STERILE RUCOLA

RELATED APPLICATIONS AND INCORPORATION BY REFERENCE

This application is a continuation-in-part application of international patent application Serial No. PCT/EP2009/054966 filed 24 Apr. 2009, which published as PCT Publication No. WO 2009/130307 on 29 Oct. 2009, which claims benefit of European patent application Serial No. 08007941.1 filed 24 Apr. 2008.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SEQUENCE LISTING

The instant application contains a Sequence Listing which has been submitted in ASCII format via EFS-Web and is hereby incorporated by reference in its entirety. Said ASCII copy, created on Dec. 10, 2010, is named 43104002.txt and is 11,695 bytes in size.

FIELD OF THE INVENTION

The invention relates to cytoplasmic male sterile Rucola or Rocket Lettuce. The invention further relates to a method of producing such cytoplasmic male sterile rocket lettuce plants and to hybrid seeds and plants produced with the male sterile plant. In addition, the invention relates to propagation material for producing the CMS plants.

BACKGROUND OF THE INVENTION

Rocket Lettuce is the commercial name for a group of species grown as Rucola. This group of species comprises *Eruca sativa, Diplotaxis tenuifolia* and *Diplotaxis muralis* plants.

The species that constitute the plant grouping known as Rucola or rocket lettuce are all cross-pollinating. *Eruca sativa, Diplotaxis tenuifolia* and *Diplotaxis muralis* are male- and female fertile and are pollinated by insects.

There is a need to develop a reliable male sterility system for 100% pure hybrid seed production of rucola. Self-pollination of (partial) fertile maternal lines will lead to F1 seed lots contaminated by selfed progeny.

It is therefore an object of the invention to provide Rucola plants that can not be propagated by selfing and that can be used for the efficient production of hybrid seeds.

Cytoplasmic male sterility is a characteristic that is transmitted by the female parent of a plant and which prohibits the formation of fertile or functional pollen. Due to the inhibition of the formation of fertile pollen, self-pollination is prohibited and all seeds produced in an F1 seed production field will efficiently be F1 hybrid seeds.

Citation or identification of any document in this application is not an admission that such document is available as prior art to the present invention.

SUMMARY OF THE INVENTION

The present invention relates to Rocket Lettuce, in particular of the species *Eruca sativa*, that contains CMS cytoplasm, in particular Ogura CMS cytoplasm, and that may be used for the efficient production of F1 Rucola seeds. Cytoplasmic male sterile Rucola plants of the invention are obtainable by a method which may comprise the steps of:

(a) providing fertile pollen from *Eruca sativa* to the stamen of plants that contain CMS cytoplasm;
(b) allowing plant embryo's to develop;
(c) isolating the embryo's;
(d) raising the embryo's in tissue culture to produce plantlets;
(e) growing plants from the plantlets;
(f) selecting plants that are male sterile and female fertile;
(g) backcrossing these plants with fertile pollen from *Eruca sativa;*
(h) selecting a plant that is male sterile and female fertile; and
(i) optionally repeating steps (g) and (h).

The plants that contain CMS cytoplasm may be suitably *Brassica oleracea plants, Brassica napus* plants or *Raphanus sativus* plants.

The CMS cytoplasm may be preferably Ogura CMS cytoplasm of *Raphanus sativus*. More preferably, the Ogura CMS cytoplasm may be improved Ogura CMS cytoplasm as found in the *Brassica oleracea* MS3a Line 00.56005, seed of which was deposited on 21 Dec. 2000 at the NCIMB in Aberdeen under deposit accession number NCIMB41037.

The Rucola plant of the invention may be an *Eruca sativa* plant. Seeds of *Eruca sativa* plants of the invention have been deposited on 20 Dec. 2006 at the NCIMB in Aberdeen under deposit accession number NCIMB41447.

The CMS as found in plants of the invention was analysed and found to be the same as the CMS found in the *Brassica* source. The results of this analysis are given in Example 3.

The invention further relates to a method for producing a male sterile Rucola plant, which may comprise the steps of:

(a) providing fertile pollen from *Eruca sativa* to the stamen of *Brassica oleracea* plants that contain CMS cytoplasm;
(b) allowing plant embryo's to develop, isolating the embryo's and raising the embryo's in tissue culture to produce plantlets;
(c) growing plants from the plantlets;
(d) selecting plants that are male sterile and female fertile;
(e) backcrossing these plants with fertile pollen from *Eruca sativa;*
(f) allowing plant embryo's to develop, isolating the 20 embryo's and raising the embryo's in tissue culture to produce plantlets;
(g) growing plants from the plantlets;
(h) selecting a plant that is male sterile and female fertile as a female parental Rucola plant; and
(i) optionally repeating steps g) and h).

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with NCIMB Ltd, Ferguson Building, Craibstone Estate, Bucksburn, Aberdeen AB21 9YA, UK, under deposit accession numbers NCIMB41037 and NCIMB41447 were made pursuant to the terms of the Budapest Treaty. Upon issuance of a patent, all restrictions upon the deposit will be removed, and the deposit is intended to meet the requirements of 37 CFR §1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: The sequences of orfB of *Brassica* (CMS/sterile) (SEQ ID NO: 1) and *Eruca sativa* (CMS) (SEQ ID NO: 8) as compared to *Eruca sativa* (fertile) (SEQ ID NO: 2).

FIG. 2: The sequences of orf138 of *Brassica* (CMS/sterile) (SEQ ID NO: 3) and *Eruca sativa* (CMS) (SEQ ID NO: 9) as compared to *Eruca sativa* (fertile) (no PCR product).

FIG. 3: The sequences of MTV7 of *Brassica* (CMS/sterile) (SEQ ID NO: 4) and *Eruca sativa* (CMS) (SEQ ID NO: 10) as compared to *Eruca sativa* (fertile) (SEQ ID NO: 5).

FIG. 4: The sequences of NAD7 of *Brassica* (CMS/sterile) (SEQ ID NO: 6) and *Eruca sativa* (CMS) (SEQ ID NO: 11) as compared to *Eruca sativa* (fertile) (SEQ ID NO: 7).

Figure 7:
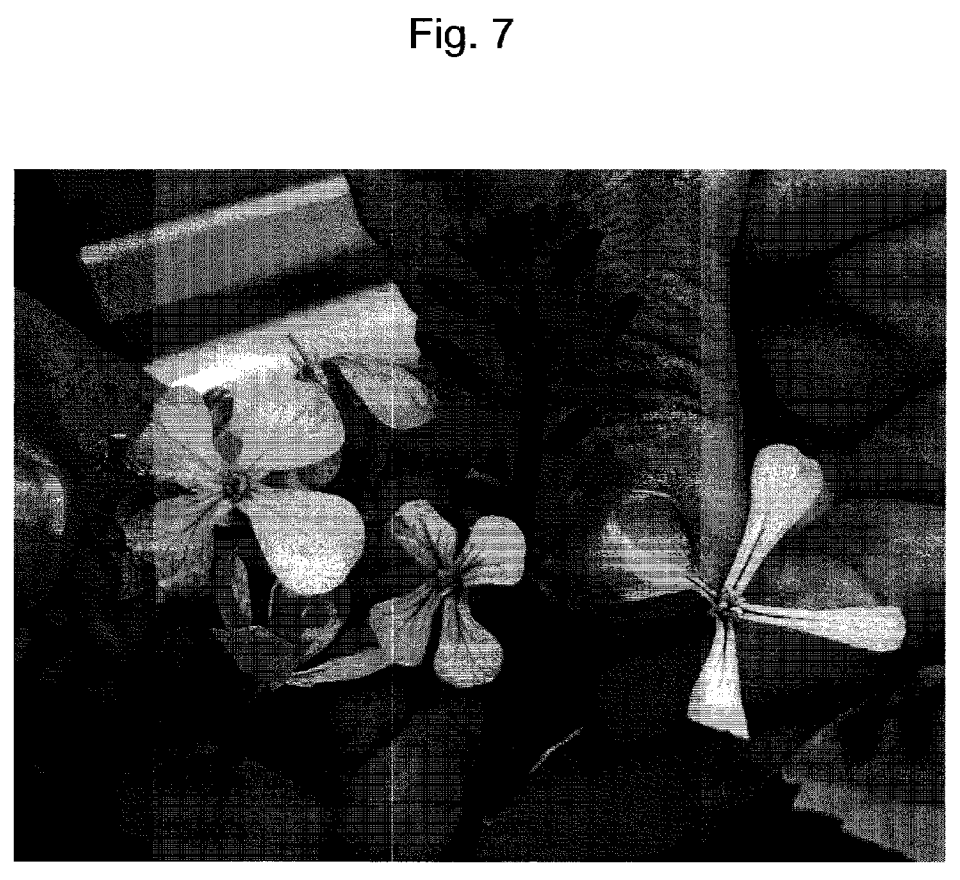

FIG. 7: Comparison between flowers of the F1 (left) and BC1 (middle) of the cross between *Eruca sativa* and *Brassica oleracea* and flowers of CMS *Brassica oleracea* (right).

FIG. 8: Flowers of CMS *Eruca sativa*.

DETAILED DESCRIPTION OF THE INVENTION

Figure 5B:
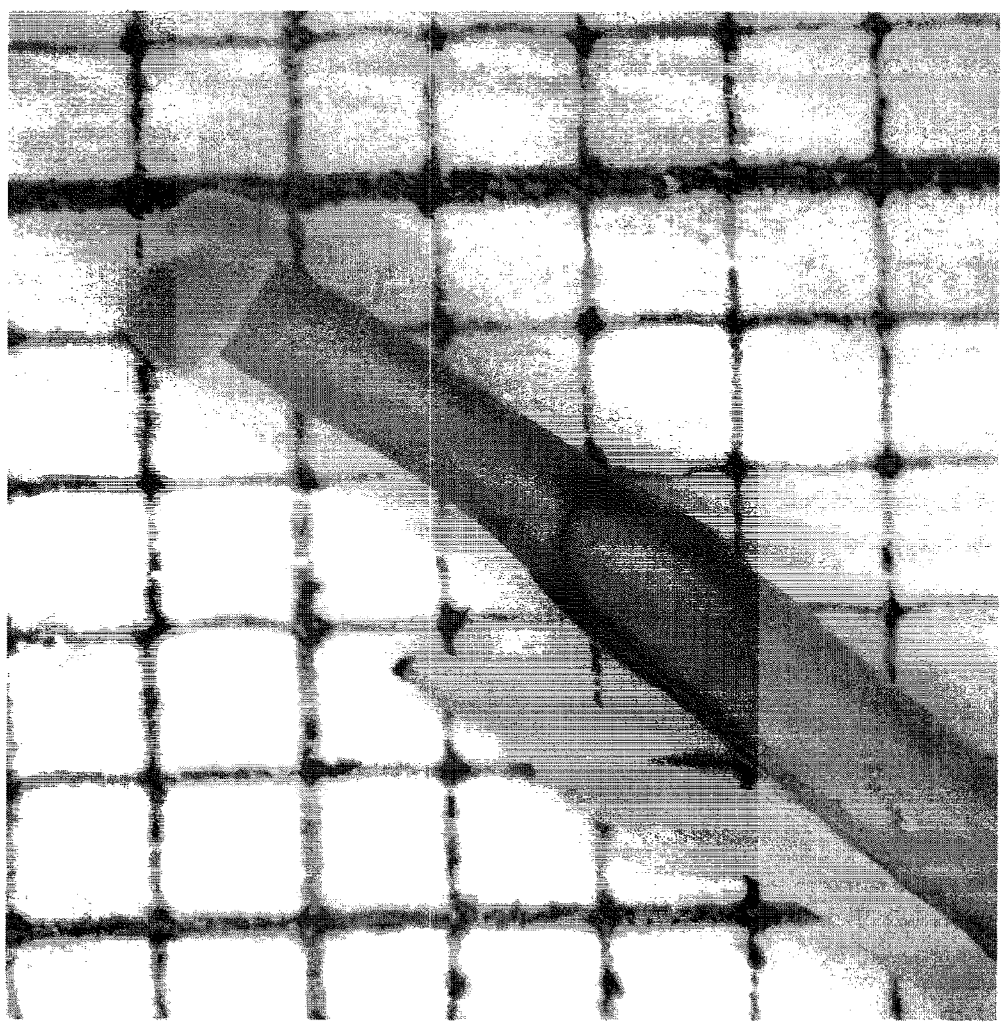
FIG. 5: A flower (A) and anthers (B) of CMS *Brassica*.

The provision of male sterile Rucola plants allows the essentially 100% pure, preferably 100% pure production of hybrid Rucola seeds by crossing a male sterile Rucola plant of the invention with a male fertile Rucola plant. Hybrids obtained by this method are also part of this invention.

The invention further relates to seeds of the male sterile Rucola plants.

The present invention provides a method for the development of 100% pure F1 hybrid seeds of Rucola. The plants of the invention contain CMS cytoplasm and show inhibition of the formation of fertile pollen.

In a preferred embodiment, the CMS cytoplasm is derived from *Brassica oleracea* plants containing the Ogura CMS cytoplasm of *Raphanus sativus. Brassica oleracea* plants containing the improved Ogura CMS cytoplasm are known to the person skilled in the art and can be prepared according to U.S. Pat. No. 5,254,802. *Brassica oleracea* varieties containing the improved Ogura CMS cytoplasm are Chambord RZ, Dexter RZ Castellum RZ.

Plants of the invention were obtained by a method in which fertile pollen grains of *Eruca sativa* were provided to the stamen of the *Brassica* plants containing the improved Ogura CMS cytoplasm. After 20 days, the embryos were isolated and raised by tissue culture under sterile conditions. Most of the plants derived from these cultures were triploid or pentaploid. Although all plants were male sterile, surprisingly, some plants were female fertile. Another backcross was performed on these plants, again using embryo rescue and tissue culture. Cytoplasmic regions (ORF138, MTV7, NAD 7, ORF-B) that are known to be related with improved Ogura CMS cytoplasm of plants derived from these tissue culture raised plants were analysed using sequencing and molecular markers.

The invention further relates to propagation material for producing plants of the invention. Such propagation material comprises inter alia seeds of the claimed plant and parts of the plant that are suitable for sexual reproduction. Such parts are for example selected from the group consisting of microspores, pollen, ovaries, ovules, embryo sacs and egg cells. In addition, the invention relates to propagation material comprising parts of the plant that are suitable for vegetative reproduction, in particular cuttings, roots, stems, cells, protoplasts.

According to a further aspect thereof the propagation material of the invention comprises a tissue culture of the claimed plant. The tissue culture comprises regenerable cells. Such tissue culture can be derived from leaves, pollen, embryos, cotyledon, hypocotyls, meristematic cells, roots, root tips, anthers, flowers, seeds and stems.

According to another aspect of the invention *Eruca sativa* plants are provided that have all of the morphological and physiological characteristics of male sterile plants of the invention, representative seed of which having been deposited under NCIMB Accession No. NCIMB41447, which plants are grown from seeds of a plant of the invention or regenerated from parts thereof, or from a tissue culture.

The invention also relates to progeny of the claimed plant. Such progeny can be produced by sexual or vegetative reproduction of a plant of the invention or a progeny plant thereof. The regenerated plant has all of the morphological and physiological characteristics of the claimed plant, representative seed of which having been deposited under NCIMB Accession Nos. NCIMB41037 and/or NCIMB41447. Such progeny has the same characteristics as claimed for the plant of the invention and may be modified in one or more other characteristics. Such additional modifications are for example effected by mutagenesis or by transformation with a transgene.

The invention furthermore relates to hybrid seed and to a method of producing hybrid seed comprising crossing a first parent plant with a second parent plant and harvesting the resultant hybrid seed that is formed on the male sterile Rucola plant, wherein said first parent plant or said second parent plant is the plant of the invention that contains CMS cytoplasm.

The invention further relates to cells of male sterile Rucola plants as described herein. The cells comprise the genetic information that leads to the cytoplasmic male sterility as described herein. Suitably, this genetic information is substantially identical, preferably completely identical to the genetic information encoding cytoplasmic male sterility of plants that have all of the morphological and physiological characteristics of male sterile plants of the invention, representative seed of which having been deposited under NCIMB Accession No. 41447. Preferably, the cell of the invention is part of a plant, but the cell may also be in isolated form.

According to a further aspect thereof the invention provides a method of producing a cultivar having the characteristics of a plant of the invention, which method comprises:

(a) crossing a mother plant with a father plant to produce a hybrid seed;
(b) growing said hybrid seed to produce a hybrid plant;
(c) selfing said hybrid seed to produce F2 progeny seed;
(d) selecting said F2 plants for having the characteristics of the invention; and
(e) optionally repeating steps (c) and (d).

In an embodiment, the invention relates to plants obtainable by crossing a first parent plant with a second parent plant that has the CMS cytoplasm trait found in plants of which representative seed was deposited under deposit accession number NCIMB41037 to obtain an F1, subsequently selfing plants of the F1 to obtain an F2 and selecting plants from the F2 that have the CMS cytoplasm trait as plants of the invention. The CMS cytoplasm trait is transferred in a pattern consistent with recessive inheritance.

Selection of plants for breeding therefore can also be independent of the phenotype of a plant and instead can be based on genetic investigations. For example, one can utilize a suitable genetic marker which is closely genetically linked to a trait of interest—the CMS cytoplasm trait in this instance, e.g., as identified using seed deposited under deposit accession number NCIMB41037. These markers can be used to identify the presence of the trait in the offspring of a particular cross (e.g., two heterozygous plants that carry the genetic information for the CMS cytoplasm trait but do not have that phenotype because it is recessive and they are not homozygous therefor), and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Methods for marker assisted selection are of particular utility in the case of recessive traits and variable phenotypes, or where conventional assays may be more expensive, time consuming or otherwise disadvantageous, and types of genetic markers which could be used in accordance with the invention include, but are not necessarily limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), and Single Nucleotide Polymorphisms (SNPs). Reference is made to U.S. Pat. No. 7,705,206, for documents and a discussion relating to the foregoing methods; and, U.S. Pat. No. 7,705,206, and the documents cited therein, including as to the foregoing methods, are hereby incorporated herein by reference consistent with the above RELATED APPLICATIONS & INCORPORATION BY REFERENCE section.

In an embodiment the second parent plant is a plant grown from the deposited seeds.

In an embodiment the second parent plant is a progeny plant of a plant grown from the deposited seeds.

In an embodiment the second parent plant is a plant having the genetic information that encodes the CMS cytoplasm phenotype.

In an embodiment this genetic information is substantially identical to the genetic information that encodes the CMS cytoplasm trait as found in plants of which representative seeds were deposited under deposit accession number NCIMB41037, in particular plants grown from seeds as deposited under deposit accession number NCIMB41037 (wherein "substantially identical" is identical to the genetic information in the seeds deposited under NCIMB41037, or so similar to the genetic information in the seeds deposited under NCIMB41037 at the locus or gene that gives rise to expression of the CMS cytoplasm trait phenotype in the seeds deposited under deposit number NCIMB41037 such that the sample also has the CMS cytoplasm trait, e.g., a sample can be "substantially identical" in its genome to seeds deposited under deposit number NCIMB41037 because it is different than the genome of seeds deposited under deposit numbers NCIMB41037 due to the degeneracy of the genetic code).

In an embodiment, the invention thus relates to a plant, showing the trait CMS cytoplasm, which plant is obtainable by:

a) growing plants representative seed of which was deposited under NCIMB41037;
b) crossing a plant from step a) with a plant that does not have the CMS cytoplasm trait to obtain an F1 population;
c) selfing plants from the F1 to obtain a F2 population; and
d) identifying plants showing the CMS cytoplasm trait in the F2 population as cytoplasmic male sterile Rucola plants.

In the method described above steps c) and d) can be repeated one or more times by selfing an Fn population to obtain an Fn+1 population and identifying plants showing the CMS cytoplasm trait in the Fn+1 population as cytoplasmic male sterile Rucola plants.

The genotype as far as it concerns the CMS cytoplasm trait is the same as or substantially similar or identical to genotype as found in the deposited seeds. On a nucleic acid molecule basis, this can mean a first nucleic acid molecule having at least about 95, 96, 97, 98 or 99 percent identity with a second nucleic molecule, wherein the second acid molecule is of a herein identified or exemplified or deposited plant, plant part, seed, cell or the like, and the expression of both the first and second nucleic acid molecules in a plant results in the phenotype of the CMS cytoplasm trait. The part of the genotype of a plant that causes the CMS cytoplasm trait will be called herein the "genetic information that encodes the CMS cytoplasm trait". Presence of this genetic information is phenotypically visible and plants having this genetic information can thus be selected on the basis of this phenotypic expression of the underlying gene or genes.

As used herein "genetic information" is intended to mean the portion of the genome, e.g. gene or genes, that are responsible for the formation of significantly more leaves; which portion of the genome can be detected in the genome, e.g. by detecting polymorphisms in the genome of "CMS cytoplasm trait" plants of which representative seed was deposited under deposit accession number NCIMB41037, and that portion of the genome, particularly the portion that gives rise to expression of the "CMS cytoplasm trait" can thus be isolated from the genome and can be an isolated nucleic acid molecule encoding the CMS cytoplasm trait (which when introduced into the genome of a regenerable cell of a plant that does not carry this genotype and when in the cell operably linked to and under the control of a suitable promoter, gives rise to the expression of the "CMS cytoplasm trait" in a plant regenerated from a tissue culture of such regenerable cells into which the isolated nucleic acid molecule has been introduced and is present in the cells operably linked to and under the control of a suitable promoter).

The presence of the genetic information that is responsible for the CMS cytoplasm trait of the invention in the genome of a plant that shows a CMS cytoplasm characteristic can be determined with the following test: The plant to be tested should be or should be made to be homozygous for the genetic information responsible for the CMS cytoplasm trait. The skilled person knows how to obtain a plant that is homozygous for the trait to be tested, e.g., via selfing or self mating or self crossing. This homozygous plant is then crossed with a tester plant that carries the genetic information that is responsible for the trait of the invention in homozygous condition. If the plant to be tested has a CMS cytoplasm characteristic as a result of the same genetic information that is responsible for the trait of the invention, all progeny plants of this first cross and successive generations will express the trait. If the CMS cytoplasm characteristic of the plant to be tested is the result of a different part of the genome, e.g. another gene or locus, segregation will occur. The tester plant can be any plant that carries the genetic information of the invention in homozygous condition, such as plants of which representative seed was deposited under accession number NCIMB41037 or plants directly grown from the deposited seeds or progeny thereof that has retained the trait.

In an embodiment of the invention a plant is provided that comprises the CMS cytoplasm trait and thus when crossed with a tester plant, that comprises the CMS cytoplasm trait of the invention and representative seed of which as deposited with the NCIMB under accession numbers a NCIMB41037, or a progeny plant thereof that comprises the CMS cytoplasm trait comprised in plants representative seed of which was deposited with the NCIMB under accession number NCIMB41037 or a plant derived therefrom and comprising the CMS cytoplasm trait, plants of the first generation progeny (F1) of said cross show a 1:0 segregation for the CMS cytoplasm trait. In both the tester plant and the plant of the invention the CMS cytoplasm trait is present in homozygous condition. plants of the second and further generations, if obtained by selfing also show a 1:0 segregation for the CMS cytoplasm trait. The tester plant can be a plant of which representative seed was deposited with the NCIMB under accession number NCIMB41037. When the genetic information responsible for the CMS cytoplasm trait as contained in the deposit is present in a plant, the plant is a plant of the invention (and seeds therefrom are seeds of the invention, plant parts thereof are plant parts of the invention, etc.).

The CMS cytoplasm characteristic of the invention has a genetic basis in the genome of the plant. With the above described cross with a tester plant, plants can be identified as being plants of the invention.

The CMS cytoplasm trait is independent of other traits of a plant. The trait can thus occur in plants that are completely different in all their other characteristics, for example in different varieties.

The deposited seeds contain in their genome the genetic information that encodes the CMS cytoplasm trait. The deposited seeds are thus a source for the genetic information that leads to the trait. The skilled person is capable of introducing the trait into any other plant he desires. A plant resulting from the initial cross between a first parent plant with a second parent plant that contains the genetic information responsible for the CMS cytoplasm trait, cannot yet be identified as being a plant of the invention. Therefore, an F2 generation is produced by selfing plants of the F1 and assessing the number of leaves of the F2 progeny plant and comparing it with the number of leaves of the first parent plant. If this number is at least 1.25 times higher than the number of leaves in the first parent plant, the progeny plant is a plant of the invention.

In one embodiment, the source from which the genetic information is acquired is formed by plants grown from the deposited seeds or sexual or vegetative descendants therefrom.

It is clear, however, that a parent that provides the trait of the invention is not necessarily a plant grown directly from the deposited seeds. For example, the parent can also be a progeny plant from the seed or a progeny plant from seeds that are identified to have or to have acquired the trait of the invention by other means.

In an embodiment, the invention relates to plants that carry the trait of the invention and have acquired said trait by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that can be introduced by backcrossing, useful traits can be introduced directly into a CMS cytoplasm trait plant of the invention, by genetic transformation techniques; and, such CMS cytoplasm plants that have additional genetic information introduced into the genome or that express additional traits by having the DNA coding therefor introduced into the genome via transformation techniques, are within the ambit of the invention, as well as uses of such plants, and the making of such plants.

Genetic transformation may therefore be used to insert a selected transgene into the plant of the invention or may, alternatively, be used for the preparation of transgenes which can be introduced by backcrossing. Methods for the transformation of plants, including, are well known to those of skill in the art.

Vectors used for the transformation of cells are not limited so long as the vector can express an inserted DNA in the cells. For example, vectors comprising promoters for constitutive gene expression in cells (e.g., cauliflower mosaic virus 35S promoter) and promoters inducible by exogenous stimuli can be used. Examples of suitable vectors include pBI binary vector. The cell" into which the vector is to be introduced includes various forms of cells, such as cultured cell suspensions, protoplasts, leaf sections, and callus. A vector can be introduced into cells by known methods, such as the polyethylene glycol method, polycation method, electroporation, *Agrobacterium*-mediated transfer, particle bombardment and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including CMS cytoplasm trait of the invention.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes can be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including plant cells, is well known in the art (See, e.g., U.S. Pat. Nos. 7,250,560 and 5,563,055).

Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from (psaD, psaF, psaE, PC, FNR, atpC, atpD, cab, rbcS) (see U.S. Pat. No. 7,161,061), the CAB-1 promoter from (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the CMS cytoplasm trait of this invention include, for example, DNA sequences or genes from another species, or even genes or sequences which originate with or are present in species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a CMS cytoplasm trait plant according to the invention. Non-limiting examples of particular genes and corresponding phenotypes one may choose to introduce into a plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.")

U.S. Pat. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above RELATED APPLICATIONS & INCORPORATION BY REFERENCE section, are additionally cited as examples of U.S. patents that may concern transformed and/or methods of transforming plants or plant cells, and techniques from these US patents, as well as promoters, vectors, etc., may be employed in the practice of this invention to introduce exogenous nucleic acid sequence(s) into the CMS cytoplasm trait (or cells thereof) of the invention, and exemplify some exogenous nucleic acid sequence(s) which can be introduced into the CMS cytoplasm (or cells thereof) of the invention, as well as techniques, promoters, vectors etc., to thereby obtain further CMS cytoplasm trait plants, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material comprises inter alia seeds of the claimed plant and parts of the plant that are suitable for sexual reproduction. Such parts are for example selected from the group consisting of seeds, microspores, pollen, ovaries, ovules, embryo sacs and egg cells. In addition, the invention relates to propagation material comprising parts of the plant that are suitable for vegetative reproduction, for example cuttings, roots, stems, cells, protoplasts.

According to a further aspect thereof the propagation material of the invention comprises a tissue culture of the claimed plant. The tissue culture comprises regenerable cells. Such tissue culture can be derived from leaves, pollen, embryos, cotyledon, hypocotyls, meristematic cells, roots, root tips, anthers, flowers, seeds and stems. (See generally U.S. Pat. No. 7,041,876 on being recognized as a plant that can be regenerated from cultured cells or tissue).

According to another aspect of the invention *Eruca sativa* plants are provided that have all of the morphological and physiological characteristics corresponding to the CMS cytoplasm trait of CMS cytoplasm plants of the invention, representative seed of which having been deposited under NCIMB Accession No NCIMB41037, which plants are grown from seeds of a plant of the invention or regenerated from parts thereof, or from a tissue culture. plants of the invention should have the morphological and physiological characteristics that correspond with the CMS cytoplasm trait but do not necessarily have all the other characteristics of plants of the deposited seeds. The trait is broadly transferable over multiple types and varieties.

The invention also relates to progeny of the plants of the invention. Such progeny can be produced by sexual or vegetative reproduction of a plant of the invention or a progeny plant thereof. The regenerated progeny plant shows the CMS cytoplasm characteristic in the same or a similar way as the plant, of which representative seed was deposited (NCIMB41037). This means that such progeny has the same characteristics as claimed for the plants of the invention. In addition to this, the plant may be modified in one or more other characteristics. Such additional modifications are for example effected by mutagenesis or by transformation with a transgene or cisgene. Alternatively, modifications in characteristics other than the CMS cytoplasm trait can be introduced by introducing the CMS cytoplasm trait in a different background.

As used herein the word "progeny" is intended to mean the offspring or the first and all further descendants from a cross with a plant of the invention that shows CMS cytoplasm characteristics. Progeny of the invention are descendants of any cross with a plant of the invention that carries the CMS cytoplasm trait.

"Progeny" also encompasses plants that carry the trait of the invention which are obtained from other plants of the invention by vegetative propagation or multiplication.

In one embodiment, the progeny plant has all of the morphological and physiological characteristics of the claimed plant in respect of the CMS cytoplasm trait, representative seed of which having been deposited under accession number NCIMB41037. Such progeny has the same CMS cytoplasm characteristics as claimed for the plant of the invention and may be modified in one or more other characteristics.

The invention further relates to cells of CMS cytoplasm plants as described herein. The cells comprise the genetic information that leads to the CMS cytoplasm trait as described herein. Suitably, this genetic information is substantially identical, preferably completely identical to the genetic information encoding the CMS cytoplasm trait of plants that have all of the morphological and physiological characteristics pertaining to the CMS cytoplasm trait of CMS cytoplasm plants of the invention, representative seed of which having been deposited under accession number NCIMB41037. Preferably, the cell of the invention is part of a plant or plant part, but the cell may also be in isolated form.

In an embodiment the plants of the invention are plants grown from seeds having the deposit accession numbers NCIMB41037 and/or NCIMB41447.

In an embodiment the plants of the invention are progeny plants of plants grown from seeds having the deposit accession number NCIMB41037 that carry the CMS cytoplasm trait.

In an embodiment the plants of the invention are plants that carry in their genome the genetic information that is responsible for the CMS cytoplasm trait by causing the plant to form significantly more leaves than a plant not having the said genetic information in its genome.

The invention, furthermore, relates to hybrid seed and to a method of producing hybrid seed comprising crossing a first parent plant with a second parent plant and harvesting the resultant hybrid seed. In order for the hybrid seed to express the trait of the invention, both parent plants need to be homozygous for the CMS cytoplasm trait but not necessarily uniform for other traits.

The invention also relates to the germplasm of plants of the invention. The germplasm is constituted by all inherited characteristics of an organism and according to the invention encompasses at least the CMS cytoplasm trait of the invention.

The invention also relates to the CMS cytoplasm leaves that are produced by the plants of the invention and marketed as vegetables, either as fresh vegetables or processed, i.e. cooked, and optionally frozen.

The invention further relates to a container comprising one or more plants of the invention in a growth substrate for harvest of leaves from the plant in a domestic environment. This way the consumer can pick very fresh leaves for use in salads. More generally, the invention includes one or more plants of the invention wherein the plant is in a ready-to-harvest condition, including with the consumer picking his own, and further including a container comprising one or more of these plants.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Pollen of Rucola (*Eruca sativa* cv. Myway) are provided to *Brassica oleracea* cv. Dexter. After 10 days, the pods are removed from the *Brassica* plants and surface sterilized (30 seconds in alcohol 70%, thereafter 5 minutes in 2.0% NaOCl, thereafter two times 10 seconds in sterile water). After sterilization, the pods are cultured in a growth chamber under 16 hr light (2.500 lux) at 25° C., in a sterile liquid Murashige & Skoog culture medium at pH 5.8 containing 3% saccharose, 300 mg/1 casein hydrolysate, 0.1 mg/1 IAA and 0.1 mg/1 kinetine. Five pods are cultured in 9 cm Petri-dishes containing 15 ml medium each. Petri-dishes are sealed using Parafilm.

After 14 days, immature embryos are isolated from the pods. 15 immature embryos are cultured in a growth chamber under 16 hr light (2.500 lux) at 21° C. in a solid Murashige & Skoog culture medium of pH 5.8 containing 2% saccharose ($MS_20$) and 8 g/1 Micro-agar.

After the immature embryos have germinated (after 1-12 weeks), growing shoots are transferred to a growth chamber under 16 hr light (2.500 lux) at 21° C. in a solid Murashige & Skoog culture medium of pH 5.8 containing 2% saccharose ($MS_20$). Every three weeks, developing plantlets are transferred to fresh $MS_20$ medium.

After the plantlets have developed four leaves, they are transferred to a jar containing solid Murashige & Skoog rooting medium at pH 6.4 containing 2% saccharose and 0.6 mg/1 IAA. The plants are further cultured in a growth chamber under 16 hr light (2.500 lux) at 21° C. After approximately 3 weeks the plants are rooted. Thereafter, plants are transferred to peat soil and transferred to a glasshouse.

Table 1 shows the results of this experiment.

TABLE 1

Interspecific crossing between CMS brassica and Rocket Lettuce

| Female parent | Pollen Donor | # Pods | # immature embryos | # potted plants |
|---|---|---|---|---|
| *Brassica oleracea* rapid cycling | *Eruca sativa* Mill. cv Myway | 105 | 16 | 12 |
| *Brassica oleracea* rapid cycling | *Eruca sativa* Mill. cv. Roquette cultivee | 220 | 95 | 20 |

Example 2

Pollen of Rucola (*Eruca sativa* cv. Myway) are provided to the F1 hybrid plants derived from Example 1.

After 10 days, the pods were removed from the F1 plants and surface sterilized (first 30 seconds in alcohol 70%, then 5 minutes in 2.0% NaOCl, and finally two times 10 seconds in sterile water). After sterilization, the pods were cultured in a growth chamber under 16 hr light (2.500 lux) at 25° C., in a sterile liquid Murashige & Skoog culture medium at pH 5.8 containing 3% saccharose, 300 mg/1 casein hydrolysate, 0.1 mg/1 IAA, 0.1 mg/1 kinetine. Five pods were cultured in 9 cm Petri-dishes containing 15 ml medium each. Petri-dishes were sealed using Parafilm.

After 14 days, immature embryos were isolated from the pods. Fifteen immature embryo's were cultured in a growth chamber under 16 hr light (2.500 lux) at 21° C. in a solid Murashige & Skoog culture medium of pH 5.8 containing 2% saccharose ($MS_20$) and 8 g/1 Micro-agar.

After the immature embryo's had germinated (after 1-12 weeks), growing shoots were transferred to a growth chamber under 16 hr light (2.500 lux) at 21° C. in a solid Murashige & Skoog culture medium of pH 5.8 containing 2% saccharose ($MS_20$). Every three weeks, developing plantlets were transferred to fresh $MS_20$ medium.

When the plantlets had developed they were transferred to a jar containing solid Murashige & Skoog rooting medium at pH 6.4 containing 2% saccharose and 0.6 mg/1 IAA. The plants were further cultured in a growth chamber under 16 hr light (2.500 lux) at 21° C. Rooting took approximately 3 weeks.

After rooting had occurred, plants were transferred to peat soil and transferred to a glasshouse.

Ploidy analysis of the plants listed in Table 2 was performed. Ploidy level of virtually all plants was triploid.

TABLE 2

10 Backcross 1 (BC1)

| Fl | Pollen Donor | #Pods | #potted plants |
|---|---|---|---|
| *Brassica* × *Eruca* cv Myway | *Eruca sativa* Mill. cv Myway | 2673 | 5 |
| *Brassica* × *Eruca* cv Roquette cultivee | *Eruca sativa* Mill. cv Roquette cultivee | 3705 | 57 |

TABLE 3

Backcross 2 (BC2)

| BC1 | Pollen Donor | # Pods | # potted plants |
|---|---|---|---|
| Myway | *Eruca sativa* Mill. cv Myway | 193 | 15 |
| Roquette cultivee | *Eruca sativa* Mill. cv Roquette cultivee | 1648 | 62 |

TABLE 4

Ploidy levels of BC2

| | ploidy level | | | | | |
|---|---|---|---|---|---|---|
| BCI | 2x | 3x | 4x | 5x | 6x | 7x |
| Myway | 1 | 2 | | | | |
| Roquette Cultivee | 25 | | | | | |

TABLE 5

Backcross 3 (BC3)

| BC2 | Pollen Donor | # Pods | # potted plants |
|---|---|---|---|
| Myway | *Eruca sativa* Mill. cv Myway | 0 | 0 |
| Roquette cultivee | *Eruca sativa* Mill. cv Roquette cultivee | 21 | 293 |

BC3 plants derived from diploid BC2 plants are phenotypically vigorous, male sterile Rucola plants and do 10 not need embryo rescue any more.

Example 3

Molecular Analysis of BC3 Plants

The sequence of Ogura related sequences in F1T2 15 plants are determined. Based on this, plants are selected having the Ogura cytoplasm.

The orf138 and orfB mitochondrial gene are known to be related specific to Ogura male-sterile cytoplasm (Yamagishi, H. and T. Terachi, *Plant Breeding* 1997, 116 (4):323-329; Terachi et al. Curr. Genet, 2001, 40(4):276-281). Sequences derived from both orf138 and orfB, as well as two randomly chosen mitochondrial genes (MTV7 and NAD7) were determined in mtDNA derived from CMS *Eruca* BC3 plants. Surprisingly, it was found that for all 4 genes, sequences in the CMS *Eruca* plants were fully identical to the sequences in the CMS *Brassica oleracea* plant that has been used as a source for the CMS plasma (FIGS. 1-4).

Example 4

CMS Phenotype in Flowers

Figure 6:
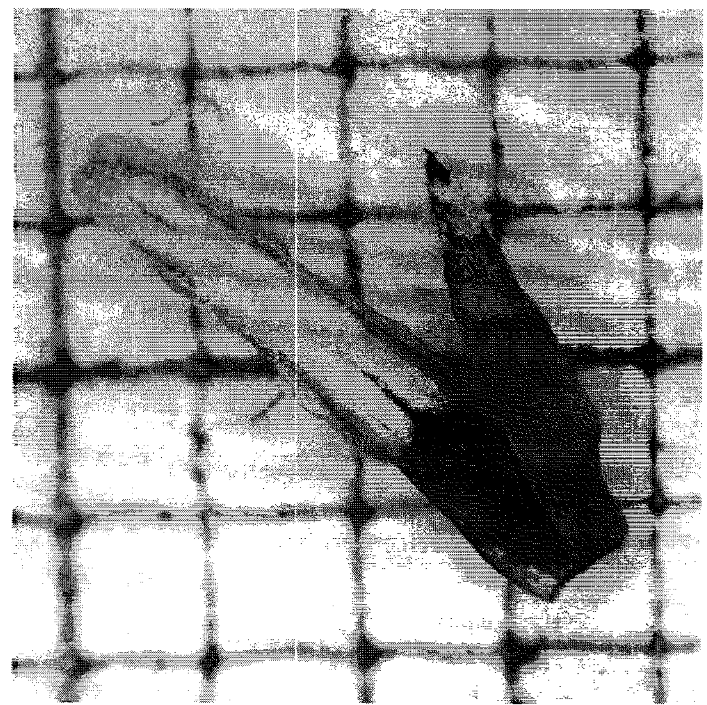
FIG. 6: Flowers (A) and anthers (B) of fertile *Eruca sativa*.

Plants derived from Example 3 are grown in the glasshouse all appeared to have a CMS phenotype. This is shown in FIGS. 5 and 6. Sterile plants have no functional anthers (FIGS. 5A and B, and 8). Anthers are under-developed and no pollen is visible.

Purity of hybrid seeds that have been produced on these plants has been determined using molecular markers. No self-pollinations have occurred.

The invention is further described by the following numbered paragraphs:

1. Male sterile Rucola plant obtainable by a method comprising the steps of:
   (a) providing fertile pollen from *Eruca sativa* to the stamen of plants that contain CMS cytoplasm,
   (b) allowing plant embryo's to develop,
   (c) isolating the embryo's,
   (d) raising the embryo's in tissue culture to produce plantlets,
   (e) growing plants from the plantlets;
   (f) selecting plants that are male sterile and female fertile;
   (g) backcrossing these plants with fertile pollen from *Eruca sativa*; and
   (h) selecting a plant that is male sterile and female fertile;
   (i) optionally repeating steps (g) and (h).

2. Rucola plant of paragraph 1, wherein the plant that contains the CMS cytoplasm is *Brassica oleracea, Brassica napus* or *Raphanus sativus.*

3. Rucola plant of paragraph 1 or 2, wherein the CMS cytoplasm is Ogura CMS cytoplasm of *Raphanus sativus.*

4. Rucola plants of paragraph 2, wherein the Ogura CMS cytoplasm is improved Ogura CMS cytoplasm as found in the *Brassica oleracea* MS3a Line 00.56005, seed of which was deposited on 21 Dec. 2000 at the NCIMB in Aberdeen under deposit accession number NCIMB41037.

5. Rucola plant of any one of the paragraphs 1-4, wherein the plant is an *Eruca sativa* plant.

6. Rucola plant of any one of the paragraphs 1-5, which plant is the *Eruca sativa* plant Mill 07.40053 seeds of which have been deposited on 20 Dec. 2006 at the NCIMB in Aberdeen under deposit accession number NCIMB41447.

7. Rucola plant of any one of the paragraphs 1-5, which plant is obtainable by crossing a parent plant with the *Eruca sativa* plant Mill 07.40053 seeds of which have been deposited on 20 Dec. 2006 at the NCIMB in Aberdeen under deposit accession number NCIMB41447.

8. Progeny plant of a plant of any one of the paragraphs 1-7.

9. Propagation material suitable for producing a plant of any one of the paragraphs 1-8, wherein the propagation material is selected from seeds, parts of the plant that are suitable for sexual reproduction, in particular microspores, pollen, ovaries, ovules, embryo sacs and egg cells, parts of the plant that are suitable for vegetative reproduction, in particular cuttings, roots, stems, cells and protoplasts, tissue cultures of regenerable cells, parts of the plant that are suitable for preparing tissue cultures, in particular leaves, pollen, embryos, cotyledon, hypocotyls, meristematic cells, roots, root tips, anthers, flowers, seeds and stems, wherein the plant produced from the propagation material contains CMS cytoplasm.

10. Plant produced from the propagation material of paragraph 9, cells of which plant contain CMS cytoplasm.

11. Cell of a plant of any one of the paragraphs 1-8 and 10, which cell comprises genetic information that leads to cytoplasmic male sterility, in particular genetic information which is substantially identical, preferably completely identical to the genetic information encoding cytoplasmic male sterility of plants that have all of the morphological and physiological characteristics of male sterile plants of the invention, representative seed of which having been deposited under NCIMB Accession No. NCIMB41447.

12. Cell of paragraph 11, which cell is part of a plant.

13. Method for producing a male sterile Rucola plant of any one of the paragraphs 1-7, comprising the steps of:
   (a) providing fertile pollen from *Eruca sativa* to the stamen of *Brassica oleracea* plants that contain CMS cytoplasm,
   (b) allowing plant embryo's to develop, isolating the embryo's and raising the embryo's in tissue culture to produce plantlets,
   (c) growing plants from the plantlets;
   (d) selecting plants that are male sterile and female fertile;
   (e) backcrossing these plants with fertile pollen from *Eruca sativa;*
   (f) allowing plant embryo's to develop, isolating the embryo's and culturing the embryo's in tissue culture to produce plantlets,
   (g) growing plants from the plantlets; and
   (h) selecting a plant that is male sterile and female fertile as a male sterile Rucola plant; and
   (i) optionally repeating steps (g) and (h).

14. Method of paragraph 13, wherein the CMS cytoplasm is Ogura CMS cytoplasm of *Raphanus sativus*, in particular improved Ogura CMS cytoplasm as found in the *Brassica oleracea* MS3a Line 00.56005, seed of which was deposited on 21 Dec. 2000 at the NCIMB in Aberdeen under deposit accession number NCIMB41037.

15. Method of any one of the paragraphs 13-14, wherein the plant is an *Eruca sativa* plant.

16. Hybrid Rucola seeds obtainable by crossing a male sterile Rucola plant of any one of the paragraphs 1-8 or 10 with a male fertile Rucola plant and harvesting the seeds formed on the male sterile Rucola plant.

17. Plants grown from seeds of paragraph 16.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A male sterile *Eruca sativa* plant having an improved Ogura cytoplasmic male sterile (CMS) cytoplasm which is found in the *Brassica oleracea* MS3a Line 00.56005, seed of which was deposited under deposit accession number NCIMB41037.

2. The male sterile *Eruca sativa* plant as claimed in claim 1, wherein the plant is the *Eruca sativa* plant Mill 07.40053 seeds of which have been deposited on 20 Dec. 2006 at the NCIMB in Aberdeen under deposit accession number NCIMB41447.

3. The male sterile *Eruca sativa* plant as claimed in claim 1, wherein the plant is obtainable by crossing a parent plant with the *Eruca sativa* plant Mill 07.40053 seeds of which have been deposited on 20 Dec. 2006 at the NCIMB in Aberdeen under deposit accession number NCIMB41447.

4. A progeny plant of the male sterile *Eruca sativa* plant as claimed in claim 1; wherein the progeny plant comprises the Ogura cytoplasmic male sterile (CMS) cytoplasm.

5. An *Eruca sativa* propagation material suitable for producing a male sterile *Eruca sativa* plant as claimed in claim 1, wherein the propagation material is selected from the group consisting of seeds; parts of the plant that are suitable for sexual reproduction; parts of the plant that are suitable for vegetative reproduction; tissue cultures of regenerable cells; and parts of the plant that are suitable for preparing tissue cultures wherein the plant produced from the propagation material contains the Ogura CMS cytoplasm.

6. An *Eruca sativa* plant produced from the propagation material as claimed in claim 5, wherein the cells of said plant produced from the propagation material contain the Ogura CMS cytoplasm.

7. Hybrid *Eruca sativa* seeds obtained by crossing the male sterile *Eruca sativa* plant as claimed in claim 1 with a male fertile *Eruca sativa* plant and harvesting the seeds formed on the male sterile *Eruca sativa* plant, wherein the seeds comprise the Ogura CMS cytoplasm.

8. Plants grown from seeds as claimed in claim 7.

9. The *Eruca sativa* propagation material of claim 5, wherein the plant parts suitable for sexual reproduction are microspores, pollen, ovaries, embryo sacs or egg cells; the plant parts suitable for vegetative reproduction are cuttings, roots, stems, cells or protoplasts; and the plant parts suitable for preparing tissue cultures are leaves, pollen, embryos, cotyledons, hypocotyls, meristematic cells, roots, root tips, anthers, flowers, seeds or stems.

10. A method for producing a male sterile *Eruca sativa* plant comprising the steps of:

(a) providing fertile pollen from *Eruca sativa* to the stamen of *Brassica oleracea* plants that contain an Ogura cytoplasmic male sterile (CMS) cytoplasm from *Raphanus sativus,*

(b) allowing plant embryos to develop, (c) isolating the embryos, (d) raising the embryos in tissue culture to produce plantlets, (e) growing plants from the plantlets;

(f) selecting plants that are male sterile and female fertile;

(g) backcrossing the selected plants from step (f) with fertile pollen from *Eruca sativa* to produce backcross progeny;

(h) selecting a backcross progeny plant from step (g) that is male sterile and female fertile; and (i) repeating steps (g) and (h), to obtain a male sterile *Eruca sativa* plant comprising the Ogura CMS cytoplasm;

wherein the Ogura CMS cytoplasm is an improved Ogura CMS cytoplasm which is found in the *Brassica oleracea* MS3a Line 00.56005, seed of which was deposited under deposit accession number NCIMB41037.

* * * * *

SEQUENCE LISTING

<160> NUMBER OF SEQ ID NOS: 11

<210> SEQ ID NO 1
<211> LENGTH: 568
<212> TYPE: DNA
<213> ORGANISM: Brassica sp.
<220> FEATURE:
<221> NAME/KEY: misc_feature
<222> LOCATION: (1)..(568)
<223> OTHER INFORMATION: OrfB sequence in Brassica (CMS/sterile)

<400> SEQUENCE: 1

```
gcacagtaga gtgctttacc taccagaggt atctatagaa tgaaagaatc attttatgct     60

tccttggcca tgtacagcat ggattagcat tatgtcattc ctacaattcc tacaagtgat    120

ccaccttcca gtatttgaag gagaggactt cgatagatta tataatatgt ttctttccat    180

tcctcgtgag ccacttattt ctccgaaaca agagatcaaa gtgattttcc tcctttttcc    240

caataagtcg acggccttac accattggga tacttcgaat aaactagcat acatatagga    300

tacaccagtg ctaaaacctt ttctcaagag atcttccaaa ctgttggggt ccttgctctg    360

gatggtcttc ccccggtgtg aaagcagttg gttccgtagt tttagaattc tgctgatccc    420

aagtactcca tctccatcat tgcatatgaa aatatagaaa gtaaagaaga aaaggcataa    480

ccagaagaat tgtgaaaaat aagtgaattt atccagttga ggcatgatta gattaattga    540

tttcaacaaa tccctccaga cagcttca                                       568
```

<210> SEQ ID NO 2
<211> LENGTH: 450
<212> TYPE: DNA
<213> ORGANISM: Eruca sativa
<220> FEATURE:
<221> NAME/KEY: misc_feature
<222> LOCATION: (1)..(450)
<223> OTHER INFORMATION: OrfB sequence in Eruca sativa (fertile)

<400> SEQUENCE: 2

```
gcggacttga cgtcatcccc caccttcctc agtatatcac tggcagtccc tcgtgagtgc     60

gtcacgcacc tttttgtttg tttcggagcg gttttgtcag ggcgtactaa acccacttcc    120

ttcgtcccac accaccgttc ggctcacctg aatgccgagt ctttctccgc cgactagtta    180

gggcttggaa aggcgccgga ggaacccctt gttactgaga gcagagctag ttgctgtcac    240

tcaattccta ggtctggcac atcactcggc tacttggctt acttcggttt gcacaacctt    300

tctccttagg cgcatgtctg agcaacacaa ggcgagggtt tcgctcgtta taggacttaa    360

ccaaacatct cacgacacga gctgacgaca gccatgcagc acctgtatga aagtcagtac    420

catcccgtta aagacaggtt ttgttgttca                                     450
```

<210> SEQ ID NO 3
<211> LENGTH: 432
<212> TYPE: DNA
<213> ORGANISM: Brassica sp.
<220> FEATURE:
<221> NAME/KEY: misc_feature
<222> LOCATION: (1)..(432)
<223> OTHER INFORMATION: Orf138 sequence in Brassica (CMS/sterile)

<400> SEQUENCE: 3

```
agtgacaata ccgcttttct tcagcatata aatgcaatga ttaccttttt cgaaaaattg     60

tccacttttt gtcataatct cactcctact gaatgtaaag ttagtgtaat aagtttcttt    120
```

```
cttttagctt ttttactaat ggcccatatt tggctaagct ggttttctaa caaccaacat    180

tgtttacgaa ccatgagaca tctagagaag ttaaaaattc catatgaatt tcagtatggg    240

tggctaggtg tcaaaattac aataaaatca aatgtaccta acgatgaagt gacgaaaaaa    300

gtctcaccta tcattaaagg ggaaatagag gggaaagagg aaaaaaaaga ggggaaaggg    360

gaaatagagg ggaaagagga aaaaaaagag gggaaagggg aaatagaggg gaaagaggaa    420

aaaaaagagg tg                                                        432


<210> SEQ ID NO 4
<211> LENGTH: 475
<212> TYPE: DNA
<213> ORGANISM: Brassica sp.
<220> FEATURE:
<221> NAME/KEY: misc_feature
<222> LOCATION: (1)..(475)
<223> OTHER INFORMATION: MTV7 sequence in Brassica (CMS/sterile)

<400> SEQUENCE: 4

gcggacttga cgtcatcccc caccttcctc agtatatcac tggcagtccc tcgtgagtgc     60

gtcacgcacc tttttgtttg tttcggagcg gttttgtcag ggcgtactaa acccacttcc    120

ttcgtcccac accaccgttc ggctcacctg aatgccgagt ctttctccgc cgactagtta    180

gggcttggaa aggcgccgga ggaacccagc ttctccccta aaggaggaac cccttgttac    240

tgagagcaga gctagttgct gtcactcaat tcctaggtct ggcacatcac tcggctactt    300

ggcttacttc ggtttgcaca acctttctcc ttaggcgcat gtctgagcaa cacaaggcga    360

gggtttcgct cgttatagga cttaaccaaa catctcacga cacgagctga cgacagccat    420

gcagcacctg tatgaaagtc agtaccatcc cgttaaagac aggttttgtt gttca         475


<210> SEQ ID NO 5
<211> LENGTH: 450
<212> TYPE: DNA
<213> ORGANISM: Eruca sativa
<220> FEATURE:
<221> NAME/KEY: misc_feature
<222> LOCATION: (1)..(450)
<223> OTHER INFORMATION: MTV7 sequence in Eruca sativa (fertile)

<400> SEQUENCE: 5

gcggacttga cgtcatcccc caccttcctc agtatatcac tggcagtccc tcgtgagtgc     60

gtcacgcacc tttttgtttg tttcggagcg gttttgtcag ggcgtactaa acccacttcc    120

ttcgtcccac accaccgttc ggctcacctg aatgccgagt ctttctccgc cgactagtta    180

gggcttggaa aggcgccgga ggaacccctt gttactgaga gcagagctag ttgctgtcac    240

tcaattccta ggtctggcac atcactcggc tacttggctt acttcggttt gcacaacctt    300

tctccttagg cgcatgtctg agcaacacaa ggcgagggtt tcgctcgtta taggacttaa    360

ccaaacatct cacgacacga gctgacgaca gccatgcagc acctgtatga aagtcagtac    420

catcccgtta aagacaggtt ttgttgttca                                     450


<210> SEQ ID NO 6
<211> LENGTH: 1080
<212> TYPE: DNA
<213> ORGANISM: Brassica sp.
<220> FEATURE:
<221> NAME/KEY: misc_feature
<222> LOCATION: (1)..(1080)
<223> OTHER INFORMATION: NAD7 sequence in Brassica (CMS/sterile)

<400> SEQUENCE: 6
```

```
ggtcgaaacg gacgaaaacg aaactttacg acagcttttt cgtacacgtt cacttgcatc     60

acatacacaa gtgctctctg aaccgtgcaa taaggtcacc cataacacgg ctctcccact    120

tgagtgattt tagccccagg ccatgctatt caatgatatt ggaaaaatgg cagcgtaacg    180

taagaactag tattgaaagc tagtcccctt ttgagggagg gaaagccttt caatagaagc    240

cctacttccc gaggtatttc ttactcgact gaaaggagag gaacgcctca tcacttcaat    300

tgttgcgcaa accaatttct ttcttagtca ccgggcggag cgcgcttttg gtactttgct    360

tatagctttt taggttatgc aatagaaggg aggcaacgct ctgggcttgc agaaatgaat    420

ggatcagaaa gagggggggg ctggattcaa tttccaggcc gggcgggagg tgaagaccat    480

aagagaagat tgccctcccg gcaaggcgtt cctcggcgtt cctcggcgct gtcatctatc    540

tcgacccatt ccctgatttt ctctgtatga ggacctcctt cccttctgcc cactctccgt    600

tcacacagtt ctcaaagcag aggaggaagg gtgggcagaa ggtaccacga gccctctgtc    660

ccacacatct atccagaagc aagtgtagtt caccggttcc accgaatgct cctatctctc    720

ggcaaagatt gtgtgagtgt gcagttatgc ttcggatgct tcgcaataga tcgacccagt    780

tcccgttctt ttccggtgca ctcgctttat atctccgata cacagggaag gacgcggtgg    840

gaaggggttc cttcgcccta gcctctgtcc ggccgatcat tccgctggca tcttgcattc    900

acgcctccgt ttgactgccg ctcggggatg tagttgtaga tacgttagtc aacgtgggtc    960

gttggctcca cctgttctct ccttctacga catgctgttg ttgtcgccat attccatatg   1020

tcacttagtc atctctgcct cgctgcgggt cagcacctcc gaaagaaacg gaggactcat   1080
```

```
<210> SEQ ID NO 7
<211> LENGTH: 1080
<212> TYPE: DNA
<213> ORGANISM: Eruca sativa
<220> FEATURE:
<221> NAME/KEY: misc_feature
<222> LOCATION: (1)..(1080)
<223> OTHER INFORMATION: NAD7 sequence in Eruca sativa (fertile)

<400> SEQUENCE: 7

ggtcgaaacg gacgaaaacg aaactttacg acagcttttt cgtacacgtt cacttgcatc     60

acatacacaa gtgctctctg aaccgtgcaa taaggtcacc cataacacgg ctctcccact    120

tgagttattt tagccccagg ccatgctatt caatgatatt ggaaaaatgg cagcgtaacg    180

taagaactag tattgaaagc tagtcccctt ttgagggagg gaaagccttt caatagaagc    240

cctacttccc gaggtatttc ttactcgact gaaaggagag gaacgcctca tcacttcaat    300

tgttgcgcaa accaatttct ttcttagtca ccgggcggag cgcgcttttg gtactttgct    360

tatagctttt taggttatgc aatagaaggg aggcaacgct ctgggcttgc agaaatgaat    420

ggatcagaaa gagggggggg ctggattcaa tttccaggtc gggcgggagg tgaagaccat    480

aagagaagat tgccctcccg gcaaggcgtt cctcggcgtt cctcggcgct gtcatctatc    540

tcgacccatt ccctgatttt ctctgtatga ggacctcctt cccttctgcc cactctccgt    600

tcacacagtt ctcaaagcag aggaggaagg gtgggcagaa ggtaccacga gccctctgtc    660

ccacacatct atccagaagc aagtgtagtt caccggttcc accgaatgct cctatctctc    720

ggcaaagatt gtgtgagtgt gcagttatgc ttcggatgct tcgcaataga tcgacccagt    780

tcccgttctt ttccggtgca ctcgctttat atctccgata cacagggaag gacgcggtgg    840

gaaggggttc cttcgcccta gcctctgtcc ggccgatcat tccgctggca tcttgcattc    900

acgcctccgt ttgactgccg ctcggggatg tagttgtaga tacgttagtc aacgtgggtc    960
```

```
gttggctcca cctgttctct ccttctacga catgctgttg ttgtcgccat attccatatg   1020

tcacttagtc atctctgcct cgctgcgggt cagcacctcc gaaagaaacg gaggactcat   1080


<210> SEQ ID NO 8
<211> LENGTH: 568
<212> TYPE: DNA
<213> ORGANISM: Eruca sativa
<220> FEATURE:
<221> NAME/KEY: misc_feature
<222> LOCATION: (1)..(568)
<223> OTHER INFORMATION: OrfB sequence in Eruca sativa (CMS)

<400> SEQUENCE: 8

gcacagtaga gtgctttacc taccagaggt atctatagaa tgaaagaatc attttatgct     60

tccttggcca tgtacagcat ggattagcat tatgtcattc ctacaattcc tacaagtgat    120

ccaccttcca gtatttgaag gagaggactt cgatagatta tataatatgt ttctttccat    180

tcctcgtgag ccacttattt ctccgaaaca agagatcaaa gtgattttcc tcctttttcc    240

caataagtcg acggccttac accattggga tacttcgaat aaactagcat acatatagga    300

tacaccagtg ctaaaacctt ttctcaagag atcttccaaa ctgttggggt ccttgctctg    360

gatggtcttc ccccggtgtg aaagcagttg gttccgtagt tttagaattc tgctgatccc    420

aagtactcca tctccatcat tgcatatgaa aatatagaaa gtaaagaaga aaaggcataa    480

ccagaagaat tgtgaaaaat aagtgaattt atccagttga ggcatgatta gattaattga    540

tttcaacaaa tccctccaga cagcttca                                       568


<210> SEQ ID NO 9
<211> LENGTH: 432
<212> TYPE: DNA
<213> ORGANISM: Eruca sativa
<220> FEATURE:
<221> NAME/KEY: misc_feature
<222> LOCATION: (1)..(432)
<223> OTHER INFORMATION: Orf138 sequence in Eruca sativa (CMS)

<400> SEQUENCE: 9

agtgacaata ccgcttttct tcagcatata aatgcaatga ttaccttttt cgaaaaattg     60

tccacttttt gtcataatct cactcctact gaatgtaaag ttagtgtaat aagtttcttt    120

cttttagctt ttttactaat ggcccatatt tggctaagct ggttttctaa caaccaacat    180

tgtttacgaa ccatgagaca tctagagaag ttaaaaattc catatgaatt tcagtatggg    240

tggctaggtg tcaaaattac aataaaatca aatgtaccta acgatgaagt gacgaaaaaa    300

gtctcaccta tcattaaagg ggaaatagag gggaaagagg aaaaaaaaga ggggaaaggg    360

gaaatagagg ggaaagagga aaaaaaagag gggaaagggg aaatagaggg gaaagaggaa    420

aaaaaagagg tg                                                        432


<210> SEQ ID NO 10
<211> LENGTH: 475
<212> TYPE: DNA
<213> ORGANISM: Eruca sativa
<220> FEATURE:
<221> NAME/KEY: misc_feature
<222> LOCATION: (1)..(475)
<223> OTHER INFORMATION: MTV7 sequence in Eruca sativa (CMS)

<400> SEQUENCE: 10

gcggacttga cgtcatcccc caccttcctc agtatatcac tggcagtccc tcgtgagtgc     60

gtcacgcacc tttttgtttg tttcggagcg gttttgtcag ggcgtactaa acccacttcc    120
```

-continued

```
ttcgtcccac accaccgttc ggctcacctg aatgccgagt ctttctccgc cgactagtta    180

gggcttggaa aggcgccgga ggaacccagc ttctcccta aaggaggaac cccttgttac    240

tgagagcaga gctagttgct gtcactcaat tcctaggtct ggcacatcac tcggctactt    300

ggcttacttc ggtttgcaca acctttctcc ttaggcgcat gtctgagcaa cacaaggcga    360

gggtttcgct cgttatagga cttaaccaaa catctcacga cacgagctga cgacagccat    420

gcagcacctg tatgaaagtc agtaccatcc cgttaaagac aggttttgtt gttca         475


<210> SEQ ID NO 11
<211> LENGTH: 1080
<212> TYPE: DNA
<213> ORGANISM: Eruca sativa
<220> FEATURE:
<221> NAME/KEY: misc_feature
<222> LOCATION: (1)..(1080)
<223> OTHER INFORMATION: NAD7 sequence in Eruca sativa (CMS)

<400> SEQUENCE: 11

ggtcgaaacg gacgaaaacg aaactttacg acagcttttt cgtacacgtt cacttgcatc     60

acatacacaa gtgctctctg aaccgtgcaa taaggtcacc cataacacgg ctctcccact    120

tgagtgattt tagccccagg ccatgctatt caatgatatt ggaaaaatgg cagcgtaacg    180

taagaactag tattgaaagc tagtcccctt ttgagggagg gaaagccttt caatagaagc    240

cctacttccc gaggtatttc ttactcgact gaaaggagag gaacgcctca tcacttcaat    300

tgttgcgcaa accaatttct ttcttagtca ccgggcggag cgcgcttttg gtactttgct    360

tatagctttt taggttatgc aatagaaggg aggcaacgct ctgggcttgc agaaatgaat    420

ggatcagaaa gagggggggg ctggattcaa tttccaggcc gggcgggagg tgaagaccat    480

aagagaagat tgccctcccg gcaaggcgtt cctcggcgtt cctcggcgct gtcatctatc    540

tcgacccatt ccctgatttt ctctgtatga ggacctcctt cccttctgcc cactctccgt    600

tcacacagtt ctcaaagcag aggaggaagg gtgggcagaa ggtaccacga gccctctgtc    660

ccacacatct atccagaagc aagtgtagtt caccggttcc accgaatgct cctatctctc    720

ggcaaagatt gtgtgagtgt gcagttatgc ttcggatgct tcgcaataga tcgacccagt    780

tcccgttctt ttccggtgca ctcgctttat atctccgata cacagggaag gacgcggtgg    840

gaaggggttc cttcgcccta gcctctgtcc ggccgatcat tccgctggca tcttgcattc    900

acgcctccgt ttgactgccg ctcggggatg tagttgtaga tacgttagtc aacgtgggtc    960

gttggctcca cctgttctct ccttctacga catgctgttg ttgtcgccat attccatatg   1020

tcacttagtc atctctgcct cgctgcgggt cagcacctcc gaaagaaacg gaggactcat   1080
```